United States Patent [19]

Simonet et al.

[11] Patent Number: 5,015,711

[45] Date of Patent: May 14, 1991

[54] THICKENING AGENT WHICH MODIFIES THE RHEOLOGICAL CHARACTERISTICS OF CHARGED AND/OR PIGMENTED, WHITE OR COLORED AQUEOUS COMPOSITIONS

[75] Inventors: Benoit Simonet, Lozanne; Pierre Fabre, Collonges-Au-Mont-D'Or; Jacques Laluet, Lyons; Jean-Bernard Egraz, Ecully, all of France

[73] Assignee: Coatex S.A., Caluire, France

[21] Appl. No.: 376,126

[22] Filed: Jul. 6, 1989

[30] Foreign Application Priority Data

Jul. 7, 1988 [FR] France ............................. 88 09509

[51] Int. Cl.$^5$ ............................................. C08F 26/02
[52] U.S. Cl. .................................. 526/301; 526/317.1; 526/318.2; 526/318.4
[58] Field of Search ................... 526/301, 302, 317.1, 526/318.4, 318.2

[56] References Cited

U.S. PATENT DOCUMENTS 4,514,552  4/1985  Shay et al. ........................ 526/301

Primary Examiner—Joseph L. Schofer
Assistant Examiner—R. H. Delmendo

Attorney, Agent, or Firm—Oblon, Spivak, McClelland, Maier & Neustadt

[57] ABSTRACT

An associative thickening copolymer, water-soluble in a neutral or alkaline medium, for charged and/or pigmented, white or colored aqueous compositions is disclosed. The copolymer is composed of (a) at least one monomer with ethylenic unsaturation having at least one carboxylic function, (b) at least one other monomer with ethylenic unsaturation without a carboxylic function, (c) at least one surfactant monomer having at least one urethane function resulting from the reaction of an isocyanate with ethylenic unsaturation with a surfactant compound having a hydroxyl function which is reactive with regard to the —NCO group, wherein said copolymer belongs to the group composed of those which, by definition, placed in aqueous solution with 2% by weight of dry material, brought to a pH of 9 by the addition of ammonia and at a temperature of 20° C., have a Brookfield viscosity at 100 revolutions per minute of at most equal to 220 centipoises.

The copolymer may be is used in charged and/or pigmented aqueous compositions such as coating compositions and, more particularly, coating colors, printing pastes, leather finishing products, cosmetic and detergent compositions and drilling fluids.

16 Claims, No Drawings

THICKENING AGENT WHICH MODIFIES THE RHEOLOGICAL CHARACTERISTICS OF CHARGED AND/OR PIGMENTED, WHITE OR COLORED AQUEOUS COMPOSITIONS

BACKGROUND OF THE INVENTION

1. Field of the Invention

The invention relates to a thickening agent which modifies the rheological characteristics of charged and-/or pigmented, white or colored aqueous compositions.

2. Discussion of the Backgrounds

For one of skill in this art, a charged and/or pigmented aqueous composition is formed from a liquid phase which can be water or a water-miscible organic solvent, or even a mixture of both, from a polymer in emulsion in the liquid phase, which is called a "binder", from charges and/or pigments, from an agent dispersing the charges and/or pigments which can be a water-soluble polymer or copolymer, from additives as varied as coalescence agents, biocidal agents, antifoaming agents or others, and finally from a thickening agent which is a natural or synthetic polymer or copolymer.

For a long time it has been shown that the presence of a thickening agent in a charged and/or pigmented aqueous composition was necessary in order to modify the rheological characteristics thereof.

Several species of thickening agents for charged and-/or pigmented aqueous compositions have been proposed to the skilled artisan and have been described abundantly in the specialized literature.

A first species of thickening agents for charged and-/or pigmented aqueous compositions consists of cellulose derivatives with the property of viscosifying only the aqueous phase of said compositions.

However, the field of application of this first species of thickening agents is limited, because disadvantages occur, causing problems to the user such as, for example, difficulties in dissolving in aqueous media, frequently slow hydration kinetics, high bacterial sensitivity, and also an inability to cause to develop, and more specifically to adjust afterwards, the viscosity of the charged and/or pigmented aqueous compositions.

Thus, it is apparent that this first species of thickening agents causes, within the charged and/or pigmented aqueous compositions in which it is used, pseudo-plastic rheological characteristics which can be troublesome, such as a high viscosity in the absence of mechanical stress which, however, decreases very considerably under the effect of shearing, resulting in poor covering power.

Another species of thickening agents has been proposed to overcome certain above-identified disadvantages of this first species. This other species is formed from synthetic latexes, which may be acrylic, illustrative descriptions of which are given for example in patents such as FR 2,131,128, FR 2,281,389, U.S. Pat. No. 2,798,053, U.S. Pat. No. 2,985,625 or even U.S. Pat. No. 2,958,679.

Thus, FR 2,281,389 describes a cross-linked polymer of maleic anhydride and ethylene in the presence of trialkyl isocyanurate, which can be used as a thickening agent for aqueous systems such as synthetic latex-based paints, mineral flocculating treatments, industrial or domestic water coagulation treatments.

In general, these thickening agents are carboxylic acid polymers with an ethylene function or copolymers of said same acids and their esters presented in the form of a low viscosity aqueous emulsion, of the oil in water type.

Soluble in aqueous and alkaline media, said thickening agents have the advantage, in relation to the above-identified cellulose derivatives, of being more easily used and of being insensitive to bacterial attacks.

However, as with the first species of thickening agents, the second species has certain disadvantages, such as causing the thickening of only the aqueous phase of said compositions, or even of conferring on said compositions rheological characteristics which are too pseudo-plastic and which are not suitable for all paint formulations.

More recently, a last species of water-soluble thickening agents has appeared in the field of charged and/or pigmented aqueous compositions. These thickening agents are traditionally called associative thickening agents, because they act not only by increasing the viscosity of the aqueous phase (by solubilization), but also by creating various bonds between the copolymer and certain components of the compositions, very probably through the appearance of hydrophobic interactions and hydrogen bonds. The advantage of these associative thickening agents, in comparison with the above-identified agents, is to provide the charged and-/or pigmented compositions in which they are used with a less pseudo-plastic behavior.

In particular, in the case of certain paints, the skilled artisan seeks to obtain a viscosity under low shearing which is fairly low so that the film deposited on the support to be protected has a tendency to level out well the irregularities in thickness due to the application (appropriate film tension), and has a viscosity under high shearing which is sufficiently high to improve the covering power and to decrease projections when said paints are applied using a roller.

This last species of associative thickening agents has been developed into two families, that of polyurethane associative thickening agents and that of acrylic associative thickening agents.

The polyurethane associative thickening agents belonging to the first family contain in their molecule one or several polyether chains terminating with hydrophobic groups, such as, for example, alkyls, aryls or alkylaryls, and are obtained by condensation chemistry.

Such agents are described in numerous patents, for example in GB 1,069,735, U.S. Pat. No. 3,770,684, U.S. Pat. No. 4,079,028 and U.S. Pat. No. 4,155,892.

However, while these agents confer on the charged and/or pigmented compositions in which they are used desirable rheological characteristics, they cause certain troublesome disadvantages for their user.

In effect these agents are in a viscous form which is not easy to handle, possibly in solution in mixtures of water and solvent(s), with the solvent possibly being more or less toxic and, thus, subject to limited use, or even has reactive incompatibility with certain components of the charged and/or pigmented compositions.

The acrylic associative thickening agents obtained by radical polymerization, belonging to the second family, which are watersoluble in a neutral or alkaline medium, are formed from copolymers in general prepared from ethylenic carboxylic acids, possibly esters of said acids and/or other monomers, and finally from at least one particular functional monomer having a lateral chain composed of polyether groups containing hydrophobic, hydrocarbon terminal radicals.

The nature of the particular functional monomer has been shown to be a determining factor in the rheological action of the charged and/or pigmented compositions containing the corresponding thickening agent.

Thus, the particular functional monomer can be a surfactant alcohol acrylate or methacrylate (EP Patent 0,013,836 and U.S. Pat. No. 4,384,096), or can result from esterification with a surfactant alcohol of acrylic acid oligomers (U.S. Pat. No. 4,421,902). This particular functional monomer can also be an oxyethyl ester of crotonic acid (U.S. Pat. No. 4,569,965), or also a maleic anhydride hemiester (EP Patent 0,248,612), or even a surfactant ether of allyl alcohol (EP Patent 0,216,479).

This particular functional monomer can finally result from the condensation of a surfactant alcohol and an unsaturated isocyanate (U.S. Pat. No. 4,514,552 and U.S. Pat. No. 4,600,761), with the presence of O—C-(O)—NH—urethane groups on the lateral chains of the copolymer providing a beneficial effect on the rheological behavior of the charged and/or pigmented compositions and in particular aqueous paints.

The object sought by the use of acrylic associative thickening agents was to modify, in the most favorable manner, the rheological characteristics of said compositions through their presence, such that they preferably have a controlled viscosity simultaneously under high and low shearing, so as to have good covering power, acceptable sag resistance and an appropriate film tension.

However, it has been noted that, among the acrylic associative thickening agents of the prior art:

certain ones already had an acceptable rheological profile, but require of large quantities to be used which the formulator desired to see decreased, the others, such as those indicated in U.S. Pat. No. 4,514,552, did not manage to control simultaneously the viscosities under high and low shearing.

SUMMARY OF THE INVENTION

In view of the above-identified disadvantages, the inventors have found and perfected an associative thickening copolymer which is water-soluble in a neutral or alkaline medium and which, as opposed to the prior art, provides the charged and/or pigmented aqueous compositions with a good state of rheological compromise under high and low shearing, which is shown by a high covering power and good film tension while retaining excellent sag resistance, both for white and colored compositions, and which uses lower quantities.

In accordance with the invention, the associative thickening copolymer which is water-soluble in a neutral or an alkaline medium, is composed:

(a) of at least one monomer having an ethylenic unsaturation site and having at least one carboxylic (i.e., —COOH) function;

(b) of at least one monomer having an ethylenic unsaturation site and without a carboxylic function; and (c) of at least one surfactant monomer having at least one urethane function resulting from the reaction of an isocyanate having an ethylenic unsaturation site with a surfactant compound having a hydroxyl function which is reactive towards the —NCO group.

The copolymer is characterized by the fact that when placed in an aqueous solution with 2% by weight of dry material at a pH of 9 obtained by the addition of ammonia and at a temperature of 20° C., has a type RVT Brookfield viscosity at 100 rpm at most equal to 220 centipoises.

DETAILED DESCRIPTION OF THE PREFERRED EMBODIMENTS

The invention relates to an associative thickening copolymer which is water-soluble in an alkaline or neutral medium and which has the property of modifying the rheological characteristics of charged and/or pigmented, white or colored aqueous compositions.

The invention also relates to the charged and/or pigmented, white or colored aqueous compositions, which desirably have a Newtonian behavior and which contain the associative thickening copolymer, whose effect on the medium simultaneously provides a good rheological compromise under high and low shearing stresses, which is shown by good characteristics of covering power and tension of the film after application, while retaining good sag resistance.

In the description of the invention, the phrase "charged and/or pigmented, white or colored aqueous compositions" defines the field of aqueous suspensions of charges and/or pigments such as, for example, coating compositions and, more especially, paints, coating colors, printing pastes, leather finishing products, compositions for cosmetics and detergents, and drilling fluids.

In addition, and more especially in the case of paints, the "covering power" characterizes the amount of paint deposited per unit of surface, the "sag resistance" defines the capability of a paint to resist running after its application on a support to be protected, and finally the "tension of the film" after application defines the ability of said paint to level the irregularities in thickness caused by its application on a support to be protected.

The associative thickening copolymer in accordance with the invention is distinguished from the known art by the fact that it provides a compromise state in said compositions and paints, leading to a balance between the extreme effects previously observed.

In other words, the associative thickening copolymer in accordance with the invention, when used in charged and/or pigmented aqueous compositions, generates media whose general rheological characteristics are close to Newtonian behavior, the viscosity of which media is increased under high shearing, and whose viscosity under low shearing is decreased in relation to the prior art, consequently improving the characteristics of covering power and film tension after the application, while retaining good sag resistance.

The Newtonian behavior of the aqueous compositions containing the associative thickening copolymer in accordance with the invention is acquired jointly due to the incorporation into its structure of a surfactant monomer having at least one urethane function and due to the fact that the molecular weight of said copolymer is very low, with the molecular weight being expressed by the measurement of the mobile 1 to 3 RVT Brookfield viscosity at 100 rpm of an aqueous solution containing 2% by weight of said dry copolymer brought to a pH of 9 by the addition of ammonia and at a temperature of 20° C., with the upper limit of the Brookfield viscosity measured under these conditions being at most 220 centipoises.

Apart from this conditional field of Brookfield viscosities as indicated above, any copolymer with the same structure, but generating a viscosity of over 220 centipoises under the conditions indicated for this measurement, results in aqueous compositions with perturbed, even bad, rheological characteristics when it is used as a thickening agent, more specifically in the case of gloss or semigloss paints.

Thus, as applicants noted, it appeared in a surprising manner that the two above-identified conditions leading to the copolymer in accordance with the invention fully cooperate, by the selection effected of low molecular weights, in creating a state of synergy enabling charged and/or pigmented, white or colored aqueous compositions to be obtained with rheological characteristics approaching Newtonian behavior.

The associative thickening copolymer in accordance with the invention is composed, as has been previously expressed, of at least three types of monomers.

The first type of monomer, (a), which is a carboxylic acid with an ethylenic unsaturation site, is a $C_{3-20}$, preferably $C_{3-12}$, compound having an ethylenic bond and at least one carboxylic group or a carboxylic acid anhydride group.

The carboxylated ethylenic monomer can be selected from among monoacids, such as acrylic acid, methacrylic acid, crotonic acid, isocrotonic acid, cinnamic acid, diacids, such as itaconic acid, fumaric acid, maleic acid, and citraconic acid, carboxylic acid anhydrides, such as maleic anhydride and diacid hemiesters, such as the $C_{1-4}$ monoesters of maleic or itaconic acids.

However, the carboxyl ethylene monomer is preferably selected from the group consisting of acrylic acid, methacrylic acid and itaconic acid.

The second type of monomer, (b), without a carboxylic function and which has ethylenic unsaturation, can be selected in a nonlimiting manner from the group consisting of acrylic or methacrylic acid esters, such as methyl, ethyl, butyl, 2-ethylhexyl and lauryl acrylates or methacrylates; ethylene glycol, propylene glycol, polyethylene glycol ($\overline{M}_n < 10^3$) and polypropylene glycol ($\overline{M}_n \leq 1.5 \times 10^3$) acrylates and methacrylates, as well as the corresponding phosphates and sulfates, acrylonitrile; acrylamide, n-methylolacrylamide; dimethylaminoethyl acrylates and methacrylates; allyl alcohol, vinyl acetate, sulfonic propane acrylamidomethyl acid, styrene and methylstyrene.

However, the second type of monomer with ethylenic unsaturation is preferably selected from among acrylic esters, such as $C_{1-4}$ alkyl acrylates and methacrylates.

The third type of monomer, which is a surfactant monomer having at least one urethane function, results from the reaction of an isocyanate with ethylenic unsaturation with a surfactant compound having a hydroxyl function which is reactive with regard to the —NCO group.

The isocyanate with ethylenic unsaturation can be prepared using the methods which are well known to the skilled artisan, such as those described for example in U.S. Pat. No. 2,718,516.

However, since these methods for preparation of the isocyanate with ethylenic unsaturation are relatively long, it is frequently preferable to use known monoisocyanates with ethylenic unsaturation such as, for example, isocyanatoethyl methacrylate (sold by Dow Chemical Company), or the meta- or para-isomers of alpha-alpha dimethylisopropylbenzylisocyanate (sold by American Cyanamid Corporation).

However, a preferred method consists of the stoichiometric dropwise addition to a $C_{2-20}$ diisocyanate, of an ethylenic compound having a single hydrogen which is active with regard to the —NCO group under the selected reaction conditions.

For the ethylenic compound, it is possible for example to use ethylene glycol, propylene glycol, polyethylene glycol and polypropylene glycol acrylates and methacrylates, allyl alcohol, allylamine, methallylamine or orthoallylphenol.

For the diisocyanate, it is possible for example to use, 1,4-tetramethylene diisocyanate, 1,6-hexamethylene diisocyanate, 2,2,4-trimethyl-1,6-diisocyanatohexane, 1,10-decamethylene diisocyanate, 4,4-methylene-bis-(isocyanatocyclohexane), 1,4-cyclohexylene diisocyanate, 1-isocyanato-3-isocyanatomethyl-3,5,5-trimethylcyclohexane, m- and p-phenylene diisocyanate, 2,4- and 2,6-toluene diisooyanate, xylene diisocyanate, 4-chloro 1,3-phenylene diisocyanate, 4,4'-methylene diphenylisocyanate, 1,5-naphthalene diisocyanate, tetrahydronaphthylene diisocyanate.

The surfactant compound having a hydroxyl function which is reactive with regard to the —NCO group of the isocyanate with ethylenic unsaturation corresponds to the general formula:

$$R_1$$

in which:

the term $(O-R_2)$ is ethylene oxide, propylene oxide, butylene oxide, or a combination of at least two of said oxygenated groups, n, which represents the average number of components $+OR_2+$ present in said surfactant, takes a value of between 5 and 150, the term $R_1$ is selected from the group composed by hydrocarbon and/or amine chemical structures, such as aliphatic or cycloaliphatic alkyls, substituted or unsubstituted aryls, polyaryls containing from 1 to 32 carbon atoms, secondary amines with the formula $(R_3)(R_4)N-$, in which $R_3$ and $R_4$ are hydrocarbon groups containing from 1 to 20 carbon atoms.

Thus, the surfactant compound provided with a hydroxyl function which is reactive with regard to the —NCO group can be preferably selected from the ethoxylated dilauryl amines, ethoxylated octyl and nonyl phenols, oxyethylated lauric, stearic or cetyl alcohols, ethoxylated mono- di- and tristyryl phenols, alone or in combination.

In a preferred embodiment, the term $R_1$ is selected from the hydrocarbon chains at $C_{12}$ to $C_{30}$, the term $-O-R_2$, from among the ethylene and/or propylene oxides and n in the range of 15 to 50.

The associative thickening copolymer in accordance with the invention contains, expressed as a percentage by weight:

(a) from 15 to 75%, and preferably from 30 to 45%, of monomer(s) with ethylenic unsaturation having at least one carboxylic function, (b) from 25 to 70%, and preferably from 45 to 60%, of other monomer(s) with ethylenic unsaturation without carboxylic function(s), (c) from 0.5 to 35%, and preferably from 4 to 15%, of surfactant monomer(s) having at least one urethane function resulting from the reaction of an isocyanate with ethylenic unsaturation with a surfactant compound having a hydroxyl function which is reactive with regard to the —NCO group, with the total of components (a), (b) and (c) being equal to 100. The associative thickening copolymer in accordance with the invention, that is having a Brookfield viscosity at 100 rpm of at most equal to 220 centipoises under the above-identified conditions, is prepared in accordance with known methods of radical copolymerization, in solution, in emulsion or in suspension, of the mixture of the above-identified monomers, in the presence of a catalytic system and known transfer agents, used in appropriate amounts, with the molecular weight of said copolymer being adjusted by means of the following methods: temperature, amount of catalyst, presence of a transfer agent or any other means or combination of means known to the skilled artisan.

The catalytic system of polymerization is desirably selected from those which are water-soluble, such as for example, sodium, potassium or ammonium persulfates, used in combination with a known reducing compound, such as for example, sodium metabisulfite.

The amount of catalytic system of polymerization can vary between 0.1% and 2% by weight of the total weight of monomers used for obtaining the copolymer in accordance with the invention.

The transfer agent is desirably selected from the alkylmercaptans, such as for example, octanethiol, decanethiol, n-dodecanethiol or t-dodecanethiol.

The amount of transfer agent can vary between 0% and 5.0% by weight in relation to the total weight of monomers present.

The copolymerization temperature can vary between 30° C. and 150° C. It is preferably selected to be lower than the lowest boiling point in the conditions of the experiment of the components present.

The copolymers in accordance with the invention develop their thickening property in an alkaline medium, in a manner such that the carboxylic functions present are totally or partially neutralized, with the neutralization agent preferably being lithium, sodium, potassium, ammonium, calcium or magnesium hydroxide, an amine or a combination of said agents.

The invention also relates to the charged and/or pigmented aqueous compositions containing the copolymer in accordance with the invention.

The charged and/or pigmented aqueous compositions are more particularly those which, white or colored, contain as principal components an aqueous phase, charges and/or pigments, a natural or synthetic binding agent and possibly, as secondary components, a dispersing agent, additives as varied as coalescence agents, biocidal agents, tensio-active agents, antifoaming agents or others and the associative thickening copolymer in accordance with the invention.

The associative thickening copolymer in accordance with the invention is added to said compositions in an amount of 0.1 to 10%, preferably in an amount of 0.1 to 5.0%, and most preferably from 0.4 to 1 5%, which quantity is expressed in percent of dry weight in relation to the total weight of the composition.

In practice, the liquid phase resulting from the copolymerization can be used in this form as an associative thickening agent, but it can also be dried by any known means to remove said phase and isolate the copolymer in the form of a fine powder and used in this other form as a associative thickening agent.

The associative thickening copolymer in accordance with the invention is used in charged and/or pigmented aqueous compositions such as coating compositions, and more particularly paints, coating colors, printing pastes, leather finishing products, compositions for cosmetics and detergents, and drilling fluids.

Having generally described this invention, a further understanding can be obtained by reference to certain specific examples which are provided herein for purposes of illustration only and are not intended to be limiting unless otherwise specified.

EXAMPLE 1

The object of this example was to illustrate the preparation of a surfactant monomer, resulting from the reaction of an isocyanate with ethylenic unsaturation on a surfactant compound having a hydroxyl function which is reactive with regard to the —NCO group.

For this purpose, the surfactant monomer was prepared in accordance with the following reaction schematic:

Step 1

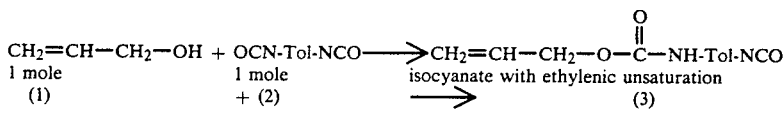

$CH_2=CH-CH_2-OH$ + $OCN\text{-Tol-NCO}$ ⟶ $CH_2=CH-CH_2-O-\overset{O}{\overset{\|}{C}}-NH\text{-Tol-NCO}$
1 mole            1 mole        isocyanate with ethylenic unsaturation
(1)              + (2)                             (3)

Step 2

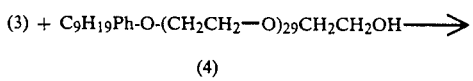

(3) + $C_9H_{19}Ph\text{-O-}(CH_2CH_2-O)_{29}CH_2CH_2OH$ ⟶

(4)

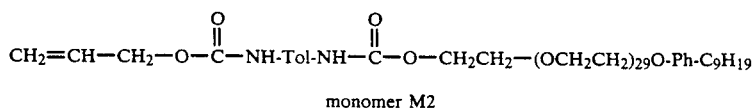

$CH_2=CH-CH_2-O-\overset{O}{\overset{\|}{C}}-NH\text{-Tol-NH}-\overset{O}{\overset{\|}{C}}-O-CH_2CH_2-(OCH_2CH_2)_{29}O\text{-Ph-}C_9H_{19}$ monomer M2

Tol: $C_6H_3-CH_3$
Ph: $C_6H_4$
(1): source of ethylenic unsaturation
(2): diisocyanate
(3): isocyanate with ethylenic unsaturation
(4): surfactant compound (alcohol)
M2: surfactant monomer with ethylenic unsaturation in which (3), which is the isocyanate with ethylenic unsaturation, reacts on (4), which is the surfactant compound.

The preparation was carried out in accordance with the following steps:

154 grams of nonyl phenol poly(ethyleneoxy)$_{29}$ ethanol and 200 grams of heptane were placed in a reactor provided with mechanical stirring and a Dean-Stark separator surmounted by a reflux condensor. The medium was then heated to 90° C. to dehydrate the surfactant. When the amount of water collected in the separator no longer varied, the heptane was distilled, first at atmospheric pressure and then under reduced pressure (5 mm Hg). The medium was then cooled and then maintained at the melting temperature of the surfactant.

17.4 grams of toluene diisocyanate, 3 drops of allooci-mene (polymerization inhibitor) and 0.24 grams of dibutyltin dilaurate (catalyst) were placed in a beaker. The beaker was placed in a water-ice bath and stirred magnetically at 50 rpm.

5.8 grams of allyl alcohol kept on a molecular sieve were placed in a dropping funnel. The allyl alcohol was poured dropwise onto the toluene diisocyanate in 30 minutes, such that the temperature of the reaction medium did not exceed 20° C. The medium was then left under stirring until the dosing of the NCO groups indicated that 50% of the isocyanate functions had reacted. The contents of the beaker were then poured in 10 minutes into the reactor containing the melted surfactant alcohol. The medium was then left under stirring for two hours. The dosing of the NCO groups then showed that all the initially present isocyanate functions had disappeared. Quantitatively in this manner, a surfactant monomer having two urethane bonds was obtained. This product is monomer M2 in Table I.

TABLE I

Preparation of surfactant monomers

| Reference of surfactant monomer | Source of ethylenic unsaturation | Diisocyanate | Surfactant alcohol R | n |
|---|---|---|---|---|
| M1 | allyl alcohol | TDI | NP | 50 |
| M2 | allyl alcohol | TDI | NP | 30 |
| M3 | allyl alcohol | TDI | NP | 17 |
| M4 | allyl alcohol | TDI | C12 | 23 |
| M5 | allyl alcohol | TDI | C12 | 17 |
| M6 | allyl alcohol | TDI | C12 | 11 |
| M7 | allyl alcohol | TDI | C16–18 | 25 |
| M8 | allyl alcohol | TDI | C16–18 | 33 |
| M9 | allyl alcohol | TDI | C16–18 | 50 |
| M10 | allyl alcohol | TDI | Distyrylphenol | 15 |
| M11 | MAEG | TDI | NP | 50 |
| M12 | MAEG | TDI | NP | 30 |
| M13 | MAEG | TDI | NP | 17 |
| M14 | MAEG | TDI | C12 | 23 |
| M15 | MAEG | TDI | C12 | 17 |
| M16 | MAEG | TDI | C12 | 11 |
| M17 | MAEG | TDI | C16–18 | 25 |
| M18 | MAEG | TDI | C16–18 | 33 |
| M19 | MAEG | TDI | C16–18 | 50 |
| M20 | MAEG | TDI | Distyrylphenol | 15 |
| M21 | MA (PEG)10 | TDI | NP | 50 |
| M22 | MA (PEG)10 | TDI | NP | 30 |
| M23 | MA (PEG)10 | TDI | NP | 17 |
| M24 | MA (PEG)10 | TDI | C12 | 23 |
| M25 | MA (PEG)10 | TDI | C12 | 17 |
| M26 | MA (PEG)10 | TDI | C12 | 11 |
| M27 | MA (PEG)10 | TDI | C16–18 | 25 |
| M28 | MA (PEG)10 | TDI | C16–18 | 33 |
| M29 | MA (PEG)10 | TDI | C16–18 | 50 |
| M30 | MA (PEG)10 | TDI | Distyrylphenol | 15 |
| M31 | Allylamine | TDI | NP | 50 |
| M32 | Allylamine | TDI | NP | 30 |
| M33 | Allylamine | TDI | NP | 17 |
| M34 | Allylamine | TDI | C12 | 23 |
| M35 | Allylamine | TDI | C12 | 17 |
| M36 | Allylamine | TDI | C12 | 11 |
| M37 | Allylamine | TDI | C16–18 | 25 |
| M38 | Allylamine | TDI | C16–18 | 33 |
| M39 | Allylamine | TDI | C16–18 | 50 |
| M40 | Allylamine | TDI | Distyrylphenol | 15 |
| M41 | AEG | TDI | NP | 50 |
| M42 | AEG | TDI | NP | 30 |
| M43 | AEG | TDI | NP | 17 |
| M44 | AEG | TDI | C12 | 23 |
| M45 | AEG | TDI | C12 | 17 |
| M46 | AEG | TDI | C12 | 11 |
| M47 | AEG | TDI | C16–18 | 25 |
| M48 | AEG | TDI | C16–18 | 33 |
| M49 | AEG | TDI | C16–18 | 50 |
| M50 | AEG | TDI | Distyrylphenol | 15 |
| M51 | m-TMI | / | NP | 50 |
| M52 | m-TMI | / | NP | 30 |
| M53 | m-TMI | / | NP | 17 |
| M54 | m-TMI | / | C12 | 23 |
| M55 | m-TMI | / | C12 | 17 |
| M56 | m-TMI | / | C12 | 11 |
| M57 | m-TMI | / | C16–18 | 25 |
| M58 | m-TMI | / | C16–18 | 33 |
| M59 | m-TMI | / | C16–18 | 50 |
| M60 | m-TMI | / | Distyrylphenol | 15 |
| M61 | IEM | / | NP | 50 |
| M62 | IEM | / | NP | 30 |
| M63 | IEM | / | NP | 17 |
| M64 | IEM | / | C12 | 23 |
| M65 | IEM | / | C12 | 17 |
| M66 | IEM | / | C12 | 11 |
| M67 | IEM | / | C16–18 | 25 |
| M68 | IEM | / | C16–18 | 33 |
| M69 | IEM | / | C16–18 | 50 |
| M70 | IEM | / | Distyrylphenol | 15 |
| M71 | allyl alcohol | IPDI | NP | 50 |
| M72 | allyl alcohol | IPDI | NP | 30 |
| M73 | allyl alcohol | IPDI | NP | 17 |
| M74 | allyl alcohol | IPDI | C12 | 23 |
| M75 | allyl alcohol | IPDI | C12 | 17 |
| M76 | allyl alcohol | IPDI | C12 | 11 |
| M77 | allyl alcohol | IPDI | C16–18 | 25 |
| M78 | allyl alcohol | IPDI | C16–18 | 33 |
| M79 | allyl alcohol | IPDI | C16–18 | 50 |
| M80 | allyl alcohol | IPDI | Distyrylphenol | 15 |
| M81 | MAEG | IPDI | NP | 50 |
| M82 | AEG | IPDI | NP | 50 |
| M83 | MA (PEG)10 | IPDI | NP | 50 |
| M84 | allylamine | IPDI | NP | 50 |
| M85 | MAEG | TDI | (C12)2-N | 50 |
| M86 | AEG | TDI | (C12)2-N | 50 |
| M87 | MA (PEG)10 | TDI | (C12)2-N | 50 |
| M88 | allylamine | TDI | (C12)2-N | 50 |

MAEG = ethylene glycol methacrylate
MA (PEG)10 = poly(ethyleneoxy)9-ethanol methacrylate
TDI = toluene diisocyanate
R = hydrocarbon radical
n = average number of ethylene oxide groups
NP = nonyl phenol radical
C12 = lauryl radical
C16–18 = ceto-stearyl radical
AEG = ethylene glycol acrylate
m-TMI = meta-isopropenyl dimethylbenzyl isocyanate
IEM = isocyanatoethyl methacrylate
IPDI = isophorone diisocyanate
(C12)2-N = dilaurylamine radical This method of synthesis was repeated using other isocyanates containing an ethylenic unsaturation and other surfactant compounds (alcohols) by adjusting the amounts of reagents so as to respect the stoichiometry of the reaction. In this manner a series of surfactant monomers cited in Table I under the references M1 to M88 were obtained.

However, in the case of monomers M51 to M70, using commercially available isocyanates with ethylenic unsaturation, step 1 of the above-identified schematic does not exist.

EXAMPLE 2

This example illustrates the preparation of an associative thickening copolymer in accordance with the invention by using the surfactant monomer M2 from Table I.

For this purpose, a pre-emulsion of monomers was first prepared by adding in order and under stirring the following compounds in the weight amounts indicated:

| | |
|---|---|
| bipermuted water | 155.00 g |
| Na ether laurylsulfate (powder) | 1.75 g |
| n-dodecanethiol | 0.95 g |
| ethyl acrylate | 147.50 g |
| surfactant monomer M2 | 25.00 g |
| methacrylic acid | 100.00 g |

In a reactor provided with a reflux condensor and mechanical stirring, the following were placed in the weight amounts indicated:

| | |
|---|---|
| bipermuted water | 506.00 g |
| Na ether laurylsulfate (powder) | 2.35 g |

The contents of the reactor were brought to 68° C. 1 gram of ammonium persulfate and 0.1 gram of sodium metabisulfite in solution in 5 grams of water were then added. The pre-emulsion of monomers was then continuously added for two hours and the temperature in the reactor was maintained at 75° C. The reaction medium was then brought to 80° for one hour and then cooled. In this manner an emulsion was obtained with 28.7% by weight of dry material of the associative thickening copolymer W of Table II. An aqueous solution with 2% of said dry copolymer brought to a pH of 9 by addition of ammonia had a viscosity of 120 cP (Brookfield RVT, mobile 2, 100 rpm, 20° C.).

This method of preparation was repeated using different surfactant monomers with ethylenic unsaturation such as were prepared in Example 1. In this manner a series of associative thickening copolymers was obtained in accordance with the invention, in emulsion form (References A to AR in Table II).

In this table and in accordance with the invention, the associative thickening copolymers placed in an aqueous solution with 2% by weight of dry material brought to a pH of 9 by the addition of ammonia and at a temperature of 20°, all had a Brookfield viscosity (RVT type) at 100 rpm of at most 220 centipoises.

TABLE II

Syntheses of copolymers in accordance with the invention

| Reference of the copolymer | Reference of the monomer Ms | % monomers Ms | AMA | AEt | % nDDT | Viscosity 2% solution with pH 9 100 rpm |
|---|---|---|---|---|---|---|
| A | M1 | 9.2 | 36.7 | 54.1 | 0.37 | 90 |
| B | M4 | 4.6 | 39.1 | 56.3 | 0.37 | 54 |
| C | M24 | 9.2 | 36.7 | 54.1 | 0.26 | 55 |
| D | M26 | 9.2 | 36.7 | 54.1 | 0.26 | 120 |
| E | M4 | 9.2 | 36.7 | 54.1 | 0.57 | 63 |
| F | M14 | 11.4 | 35.8 | 52.8 | 0.18 | 116 |
| G | M4 | 11.4 | 35.8 | 52.8 | 0.47 | 100 |
| H | M14 | 9.2 | 36.7 | 54.1 | 0.28 | 72 |
| I | M6 | 9.4 | 37.8 | 52.8 | 0.87 | 47 |
| J | M6 | 9.4 | 37.8 | 52.8 | 0.66 | 85 |
| K | M5 | 9.2 | 36.7 | 54.1 | 0.61 | 82 |
| L | M7 | 9.2 | 36.7 | 54.1 | 0.83 | 71 |
| M | M8 | 9.2 | 36.7 | 54.1 | 0.60 | 41 |
| N | M8 | 9.2 | 36.7 | 54.1 | 0.49 | 57 |
| P | M6 | 9.2 | 36.7 | 54.1 | 0.66 | 87 |
| Q | M8 | 9.2 | 36.7 | 54.1 | 0.39 | 90 |
| R | M4 | 9.2 | 36.7 | 54.1 | 0.50 | 70 |
| S | M8 | 9.2 | 36.7 | 54.1 | 0.50 | 58 |
| T | M3 | 9.2 | 36.7 | 54.1 | 0.40 | 156 |
| U | M9 | 9.2 | 36.7 | 54.1 | 0.40 | 132 |
| V | M3 | 9.2 | 36.7 | 54.1 | 0.60 | 65 |
| W | M2 | 9.2 | 36.7 | 54.1 | 0.35 | 120 |
| X | M1 | 9.2 | 36.7 | 54.1 | 0.59 | 70 |
| Y | M2 | 9.2 | 36.7 | 54.1 | 0.50 | 77 |
| Z | M1 | 9.2 | 36.7 | 54.1 | 0.40 | 88 |
| AA | M14 | 4.3 | 36.1 | 59.6 | 0.26 | 95 |
| AB | M14 | 6.9 | 37.6 | 55.5 | 0.28 | 59 |
| AC | M14 | 13.8 | 34.8 | 51.4 | 0.28 | 73 |
| AD | M14 | 11.5 | 35.7 | 52.7 | 0.18 | 99 |
| AE | M14 | 9.2 | 36.7 | 54.1 | 0.13 | 208 |
| AF | M34 | 9.2 | 36.7 | 54.1 | 0.50 | 45 |
| AG | M10 | 9.2 | 36.7 | 54.1 | 0.50 | 132 |
| AH | M14 | 10.0 | 30.0 | 60.0 | 0.28 | 67 |
| AI | M14 | 10.0 | 20.0 | 70.0 | 0.28 | 41 |
| AJ | M14 | 10.0 | 40.0 | 50.0 | 0.28 | 82 |
| AK | M14 | 10.0 | 55.0 | 30.0 | 0.28 | 87 |
| AL | M14 | 10.0 | 45.0 | 45.0 | 0.28 | 78 |
| AM | M14 | 15.0 | 15.0 | 70.0 | 0.28 | 30 |
| AN | M14 | 14.3 | 23.8 | 61.9 | 0.28 | 37 |
| AP | M14 | 20.0 | 30.0 | 50.0 | 0.28 | 91 |
| AQ | M14 | 5.0 | 55.0 | 40.0 | 0.28 | 65 |
| AR | M54 | 9.2 | 36.7 | 54.1 | 0.15 | 58 |

AMA = methacrylic acid
AEt = ethyl acrylate
MS = surfactant monomer
nDDT = n-dodecanethiol

EXAMPLE 3

The object of this example is to compare associative thickening copolymers, objects of the invention taken from Table II, with prior art associative thickening agents sold commercially.

Among the associative thickening agents of the prior art, three of them, reputed to be among the best, were selected for this comparative study.

The first one, called "alpha" in the following text, is Primal RM5, sold by Rohm & Haas Company.

The second one, called "beta" in the following text, is Viscalex VG2, sold by Allied Colloids Company.

The third one, called "gamma" in the following text is Mowilith LDM 7000, sold by Hoechst Company.

For this purpose, a series of gloss, white aqueous paints was prepared in which only the type and amount of associative thickening agent changed.

These paints were formulated from an orientation formula proposed by the producers of binding agents to the formulators for the binding agent used conventionally in this type of paint.

The quantities of the components of said paints, except for the thickening agents which are the objects of the comparison, were expressed in grams, while the quantities of thickening agent was expressed in percentages of dry polymer in relation to the total of each formulation.

The formulations used are listed in Table III-A and the results in Table III-B.

To use the results in Table III-B, it is desirable to define the methods and/or means used to obtain said results.

Viscosity 24 hours

This viscosity was measured in a systematic manner 24 hours after producing each white paint.

The measurement was taken using a Brookfield RVT viscosimeter at 20° C. using a mobile selected so as to obtain an index deviation within the graduation range 15 to 80. The value obtained is representative of the viscosity of said paints in the can (viscosity under low shearing).

Apparent Viscosity

This measurement was taken using a Contraves (trademark) Rheomat 30 rheometer.

For this purpose, a small quantity of paint was placed in the air gap (50 μm) of a mobile HS 50, and the shearing stress curve ($\tau$) was recorded as a function of the shear rate (D). The apparent viscosity was the ratio of $\tau/D$ for D=17700 s-1.

The shearing at 17700 s-1 is representative of the high shearings encountered during the application of paints with a brush or a roller. The apparent viscosity measure therefore appeared to be a means of observing how the paint would act using a brush or a roller.

Yield Value

This measurement was also carried out using a Contraves (trademark) Rheomat 30 rheometer using a DIN 25 mobile.

TABLE III-A

| | | Thickening agent | | | | | | |
|---|---|---|---|---|---|---|---|---|
| | | alpha | beta | gamma | H | H | E | G |
| | | | | Reference | white paint | | | |
| | | 3-1 | 3-2 | 3-3 | 3-4 | 3-5 | 3-6 | 3-7 |
| White paint formula: coalescent: | | | | | | | | |
| propylene glycol | 50.20 | | | | | | | |
| water | 42.00 | | | | | | | |
| dispersant: Coatex BR3 (a) | 4.20 | | | | | | | |
| bactericide: Mergal K6N (b) | 2.50 | | | | | | | |
| antifoaming agent: Nopco NDW (c) | 0.80 | | | | | | | |
| pigment: TiO2 RHD2 (d) | 196.60 | | | | | | | |
| binding agent: Primal HG 74 (e) | 568.50 | | | | | | | |
| coalescent: methoxybutanol | 25.10 | | | | | | | |
| coalescent: Texanol (f) | 36.20 | | | | | | | |
| ammonia (28%) | 3.00 | | | | | | | |
| thickening agent (% dry/ total formula) | | 0.82 | 0.82 | 0.82 | 0.82 | 0.62 | 0.82 | 0.82 |
| antifoaming agent: Nopco NDW | 0.80 | | | | | | | |
| ammonia (28%) quantity sufficient for pH | 8.7 | | | | | | | |
| water quantity sufficient for total | 1000 | | | | | | | |
| total | 1000.00 | | | | | | | |

(a) sold by Coatex (France)
(b) sold by Omya (France)
(c) sold by Henkel (FRG)
(d) sold by Tioxide (GB)
(e) sold by Rohm & Haas (USA)
(f) sold by Eastman Chemicals (USA)

To carry out this measurement of yield value, the paint was first subjected to considerable shearing (approximately 500 s-1) so as to destructure it. Then, the curve was recorded: shearing stress as a function of the shear rate (D), with said rate varying from 0 to 5 s-1. The intersection of the tangent at the low part of the curve with the axis of shearing stresses gives the yield value.

Film Tension

The film tension after application defines the capability of the paints to level out the irregularities in thickness caused by their application onto a support to be protected. In order to take the measurement, a simulation of the irregularities was carried out by depositing onto a glass plate five pairs of cords with an initial rectangular cross-section, with each pair being 2 millimeters apart. The thickness of the cords was 0.25 millimeters, 0.50 millimeters, 1 millimeter, 2 millimeters and 4 millimeters. The plate was kept horizontal. After drying, the number of pairs of deposits where the cords became joined was noted. The best film tension was therefore 5, that is all the pairs of cords became joined, and the worst was 0, that is no pair became joined.

Sag resistance defines the capability of a paint to resist sag after its application on a support to be protected.

To carry out the measurement, using a gauge 10 cords of a width of 6 millimeters and thicknesses of between 75 and 300 microns, in increments of 25 microns, were deposited on a glass plate, with the different deposits being separated by a distance of 2 millimeters. The plate was then placed vertically, with the thickest deposits being placed at the bottom. After drying, the number of unjoined bands was noted. The best sag resistance was therefore 10 and the worst was 0.

The last two measurements of film tension and sag resistance were carried out in accordance with standard ASTM D 280169.

Gloss

The measurement of the gloss, the technique of which is well known to the skilled artisan, was carried out using an Erichsen (trademark) glossmeter on dry film after 24 hours.

Application

After applying the paint with a brush onto a kraft-type support, the operator judged, using his know-how, three qualities of application, which were the brushability, the film tension and the covering power in accordance with the following notations:

| brushability | A = excellent |
| --- | --- |
| | B = good |
| | C = average |
| | D = difficult to apply |
| | E = very difficult to apply | with the brushability indicating the more or less agreeable sensation which the user feels during the application of the film.

| film tension | A = excellent |
| --- | --- |
| | B = good |
| | C = stretches fairly well |
| | D = cords a little |
| | E = cords a lot |
| covering power | A = covers very well |
| | B = covers well |
| | C = covers fairly well |
| | D = covers little |
| | E = covers badly |

All the results relative to the above-identified tests have been assembled in Table III-B.

TABLE III-B

| | Thickening agent (% dry/total formula) | | | | | | |
| --- | --- | --- | --- | --- | --- | --- | --- |
| | alpha 0.82 | beta 0.82 | gamma 0.82 | H 0.82 | H 0.62 | E 0.82 | G 0.82 |
| | Reference white paint | | | | | | |
| | 3-1 | 3-2 | 3-3 | 3-4 | 3-5 | 3-6 | 3-7 |
| pH | 8.7 | 8.7 | 8.8 | 8.7 | 8.7 | 8.7 | 8.7 |
| Brookfield viscosity | | | | | | | |
| 10 rpm | 2800 | 11800 | 11600 | 7200 | 6000 | 4500 | 6800 |
| 24 hours (cP) 100 rpm | 1600 | 2650 | 3300 | 3880 | 3440 | 2780 | 3840 |
| Apparent viscosity (mPa.s) | 186 | 130 | 191 | 331 | 222 | 209 | 241 |
| Yield value (pa) | 1.30 | 12.50 | 11.00 | 3.20 | 2.20 | 1.30 | 2.10 |
| Film tension | 3 | 2 | 2 | 2 | 3 | 3 | 3 |
| Sag Resistance | 2 | 9 | 9 | 9 | 7 | 8 | 9 |
| Gloss (%) 20° | 68 | 67 | 71 | 67 | 68 | 65 | 67 |
| 24 hours 60° | 85 | 85 | 87 | 86 | 85 | 84 | 86 |
| 85° | 95 | 94 | 96 | 95 | 95 | 94 | 94 |
| Application: | | | | | | | |
| brushability | D | D | C | C | B | A | B |
| film tension | C | E | D | B | B | B | B |
| covering power | C | E | C | A | A | B | A |

From Table III-B it can be noted that the apparent viscosity of the paints thickened using associative copolymers in accordance with the invention is always greater than 200 mPa.s, whereas the apparent viscosity of paints thickened using currently sold thickening agents of the prior art is always beneath 200 mPa.s, with a constant amount of thickening agent.

In the case of paint 3-4 (object of the invention), the apparent viscosity is 70% higher than the best apparent viscosity of the prior art paints.

In the case of paints 3-1 to 3—3, which represent the prior art, it can be noted that:

for paint 3-1, the viscosity at 24 hours is too low and leads to mediocre sag resistance, for paints 3-2 and 3—3, this viscosity at 24 hours is too high and leads to too great a yield value, resulting in bad film tension (cording effect).

In the case of paints 3-4 and 3-5, which are the objects of the invention, the decrease in amount of thickening agent (24% less in relation to the prior art) enables the apparent viscosity to be maintained at a favorable level, still above 200 mPa.s while decreasing the viscosity at 24 hours and the yield value enables, without harming the covering power, to improve the film tension as well as the brushability.

With regard to paints 3-6 and 3-7, which are also objects of the invention, they offer rheological and application characteristics which are better than the characteristics of the prior art.

EXAMPLE 4

The object of this example is to compare the associative thickening copolymers, objects of the invention from Table II, with commercially available associative thickening agents belonging to the prior art.

The three agents alpha, beta and gamma defined in Example 3 were used as the associative thickening agents of the prior art.

The formulations of these paints were carried out from an orientation formula proposed by the binding agent manufacturers to the formulators for the binding agent used and conventional in this type of paint.

The quantities of the components of said paints, except for the thickening agents which are the objects of the comparison, were expressed in grams, while the quantity of thickening agents were expressed as a percentage of dry polymer in relation to the total for each formulation.

The formulations used are shown in Table IV-A and the results in Table IV-B.

TABLE IV-A

|  |  | Thickening agent | | | | |
|---|---|---|---|---|---|---|
|  |  | gamma | beta | alpha | H | H |
|  |  |  |  | Reference white paint |  |  |
|  |  | 4-1 | 4-2 | 4-3 | 4-4 | 4-5 |
| White paint formula |  |  |  |  |  |  |
| Water | 25.00 |  |  |  |  |  |
| dispersing agent: Coatex BR3 (a) | 4.00 |  |  |  |  |  |
| antifoaming agent: Tego Foamex 1488 (b) | 0.80 |  |  |  |  |  |
| bactericide: Mergal K6N (c) | 2.20 |  |  |  |  |  |
| coalescent: propylene glycol | 25.00 |  |  |  |  |  |
| pigment: TiO2 RHD2 (d) | 210.00 |  |  |  |  |  |
| binding agent: Mowilith LDM 7770 (e) | 600.00 |  |  |  |  |  |
| coalescent: propylene glycol coalescent: | 75.00 |  |  |  |  |  |
| Texanol (f) | 15.00 |  |  |  |  |  |
| ammonia (28%) | 4.40 |  |  |  |  |  |
| thickening agent (% dry/total formula) |  | 0.58 | 0.58 | 0.58 | 0.58 | 0.43 |
| water quantity sufficient for total | 1024 |  |  |  |  |  |
| ammonia (28%) quantity sufficient for pH | 8.7 |  |  |  |  |  |
| Total | 1024.00 |  |  |  |  |  |

(a) sold by Coatex (France)
(b) sold by Tego Chemie (FRG)
(c) sold by Omya (France)
(d) sold by Tioxide (GB)
(e) sold by Hoechst (FRG)
(f) sold by Eastman Chemicals The tests listed in Table IV-B were carried out in accordance with the definitions given in Example 3.

All the results relative to the above-identified tests are assembled in Table IV-B.

TABLE IV-B

|  | Thickening agent (% dry/total formula) | | | | |
|---|---|---|---|---|---|
|  | gamma | beta | alpha | H | H |
|  | 0.58 | 0.58 | 0.58 | 0.58 | 0.43 |
|  |  |  | Reference white paint |  |  |
|  | 4-1 | 4-2 | 4-3 | 4-4 | 4-5 |
| pH | 8.7 | 8.7 | 8.7 | 8.7 | 8.7 |
| Brookfield viscosity: 10 rpm | 4800 | 1600 | 2600 | 6000 | 3400 |
| 24 hours (cP) 100 rpm | 1440 | 740 | 1280 | 2840 | 1800 |
| Apparent viscosity (mPa.s) | 149 | 86 | 122 | 214 | 161 |
| Yield value (Pa) | 1.00 | 0.50 | 0.10 | 2.30 | 0.80 |
| Film tension | 3 | 5 | 5 | 4 | 4 |
| Sag resistance | 5 | 0 | 1 | 7 | 7 |
| Gloss (%) 20 | 59 | 60 | 64 | 64 | 61 |

TABLE IV-B-continued

| | Thickening agent (% dry/total formula) | | | | |
|---|---|---|---|---|---|
| | gamma 0.58 | beta 0.58 | alpha 0.58 | H 0.58 | H 0.43 |
| | Reference white paint | | | | |
| | 4-1 | 4-2 | 4-3 | 4-4 | 4-5 |
| 24 hours 60 | 73 | 75 | 79 | 81 | 80 |
| 85 | 75 | 78 | 81 | 84 | 87 |
| Application: | | | | | |
| brushability | B | E | E | A | B |
| film tension | C | B | A | A | A |
| covering power | C | E | D | A | B |

Table IV-B shows, in combination with Table III-B, the evident superiority of the associative thickening agent H in accordance with the invention. In effect, for identical amount of thickening agent, the apparent viscosity of paint 4—4 (object of the invention) is 40% better than the best apparent viscosity of the relative prior art paints (4-1 to 4-3).

In the case of paints 4—4 and 4-5, which comprise the object of the invention, the decrease of 26% in the amount of thickening agent (paint 4-5) leads to a paint whose rheology and application characteristics are always better than those of the relative known art paints (4-1 to 4-3).

The three agents, alpha, beta and gamma, defined in Example 3 were used as the known art associative thickening agents.

These paints were formulated from an orientation formula proposed by the binding agent producers to the formulators for the binding agent used conventionally in this type of paint.

The quantities of the components of said paints, except for the thickening agents which are the objects of the comparison, are expressed in grams, while the quantity of thickening agent is expressed as a percentage of dry polymer in relation to the total of each formulation.

The formulations used have been assembled in Table V-A and the results of the tests in Table V-B.

TABLE V-A

| | | Thickening agent | | | | | |
|---|---|---|---|---|---|---|---|
| | | alpha | beta | beta | gamma | gamma | H |
| | | Reference white paint | | | | | |
| | | 5-1 | 5-2 | 5-3 | 5-4 | 5-5 | 5-6 |
| White paint formula: | | | | | | | |
| coalescent: | | | | | | | |
| propylene glycol | 24.30 | | | | | | |
| water | 31.80 | | | | | | |
| dispersant: | 4.00 | | | | | | |
| Coatex BR3 (a) | | | | | | | |
| bactericide: | 1.50 | | | | | | |
| Mergal K6N (b) | | | | | | | |
| antifoaming agent: | 1.00 | | | | | | |
| Byk 073 (c) | | | | | | | |
| pigment: | | | | | | | |
| TiO2 RHD2 (d) | 230.30 | | | | | | |
| ammonia (28%) | 2.50 | | | | | | |
| coalescent: | 24.50 | | | | | | |
| ethyl diglycol | | | | | | | |
| coalescent: | 24.50 | | | | | | |
| butyl diglycol | | | | | | | |
| binding agent: | 580.60 | | | | | | |
| Neocryl XK 76 (e) | | | | | | | |
| thickening agent (% dry/ total formula) | | 1.10 | 0.50 | 1.10 | 0.40 | 1.10 | 1.10 |
| water quantity sufficient for total | 1000 | | | | | | |
| antifoaming agent: | | | | | | | |
| Byk 073 | 1.00 | | | | | | |
| ammonia (28% quantity sufficient for pH | 8.7 | | | | | | |
| total | 1000.00 | | | | | | |

(a) sold by Coatex (France)
(b) sold by Omya (France)
(c) sold by Byk Chemie (FRG)
(d) sold by Tioxide (GB)
(e) sold by Polyvinyl Chemie (Netherlands)

EXAMPLE 5

The object of this example is to compare associative thickening copolymers, objects of the invention taken from Table II, with commercially available associative thickening agents belonging to the prior art.

The tests listed in Table V-B were carried out in accordance with the definitions which have been given of same in Example 3.

All the results relative to the above-identified tests are assembled in Table V-B.

TABLE V-B

| | Thickening agent (% dry/total formula) | | | | | |
|---|---|---|---|---|---|---|
| | alpha 1.10 | beta 0.50 | beta 1.10 | gamma 0.40 | gamma 1.10 | H 1.10 |
| | Reference white paint | | | | | |
| | 5-1 | 5-2 | 5-3 | 5-4 | 5-5 | 5-6 |
| pH | 8.7 | 8.7 | 8.7 | 8.7 | 8.7 | 8.7 |
| Brookfield viscosity: | | | | | | |
| 10 rpm | 5000 | 4000 | 9500 | 3400 | 13300 | 3600 |
| 24 hours (cP) 100 rpm | 1720 | 1040 | 2570 | 760 | 2960 | 2320 |
| Apparent viscosity (mPa.s) | 172 | 65 | 153 | 61 | 186 | 245 |
| Yield value (pa) | 2.00 | 6.00 | 6.30 | 4.20 | 11.20 | 1.50 |
| Film tension | 3 | 1 | 3 | 3 | 0 | 3 |
| Sag Resistance | 7 | 8 | 9 | 7 | 9 | 6 |
| Gloss 20° | 54 | 53 | 56 | 52 | 57 | 54 |
| 24 hours 60° | 76 | 75 | 78 | 73 | 77 | 76 |
| 85° | 84 | 87 | 88 | 84 | 89 | 88 |
| Application: | | | | | | |
| brushability | C | D | C | D | C | A |
| film tension | C | D | E | C | E | A |
| covering power | A | E | B | E | B | A |

Table V-B shows that, in accordance with Tables III-B and IV-B, the paint formulated with the associative thickening agent in accordance with the invention (5-6) in an amount of 1.1% in relation to the total weight of the formula, has an apparent viscosity which is 30% better than the best apparent viscosity of paints relative to the prior art (5-1, 5-3 and 5—5) for a same amount of dry thickening agent.

In addition, in the case of paints 5-3 and 5—5 relative to the known art, the viscosities at 24 hours (in the can) are too high, creating yield values which are too great and which affect the film tension.

With a view to overcoming this phenomenon, decreasing the amount of thickening agent (references 5-2 and 5-4) causes a reasonable drop in the viscosity at 24 hours, but a considerable fall in apparent viscosity, with as a consequence the unacceptable decrease in covering power.

Consequently, from Examples 3, 4 and 5, it is apparent that the acrylic associative thickening agents in accordance with the invention provide the paints in which they are used with rheological and application characteristics which are always better than those of the paints thickened using commercial thickening agents which are reputed to be among the best.

These agents provide the paints not only with a considerable covering power (high apparent viscosity) but also with an excellent compromise between the film tension and the sag resistance, which characteristics are naturally contrary to one another.

In addition, these agents can be used in amounts which are lower than those of the prior art thickening agents, while retaining for the paints containing them better rheology and application characteristics than those of paints formulated with the thickening agents of the prior art.

Finally, the thickening agents in accordance with the invention show, through the examples, that they provide the paints containing them with rheological and application characteristics which are not noticed in the paints formulated using thickening agents of the known art.

EXAMPLE 6

The object of this example is to illustrate the influence of the molecular weight of the associative thickening agent on its ability to be used in a formulation in a gloss aqueous paint.

The object of this example is more particularly to prove that the molecular weight of said thickening agent must be less than a limit value in order for it to retain its ability to be used in said paints, with said limit value expressed in Brookfield viscosity being at most equal to 220 centipoises for an aqueous solution with 2% of the dry thickening agent brought to a pH of 9 by the addition of ammonia, at a temperature of 20° C., for a speed of 100 rpm and a mobile providing an index deviation of between 15 and 80 at the moment of measurement.

In this example, the measurement of the RVT Brookfield viscosity relative to the molecular weight of each associative thickening agent tested is carried out, not only at a concentration of 2%, but also at a concentration of 1% of the dry thickening agent in accordance with the method of measurement described in U.S. Pat. No. 4,514,552 so as to have a common means of measurement enabling the comparison of the thickening agents in accordance with the invention with the thickening agents of the prior art described in said patent.

For this purpose, paints were prepared in accordance quantitatively and qualitatively with test 3-5 of Example 3, that is with the same binding agent, which is Primal HG 74 from Rohm & Haas.

Paints 6-1 and 6-3 contained thickening agents of the known art, and paints 6-5 and 6—6 contained thickening agents in accordance with the invention, with said thickening agents being used at a rate of 0.62% of dry product in relation to the total of the formula.

Paints 6-2 and 6-4 contained thickening agents of the known art, but in lower amounts.

The results relative to the above-identified paints and to the tests carried out on said paints, such as defined in Example 3, have been assembled in Table VI.

TABLE VI

| Selection of the molecular weights adapted to the formulation of paints on the formula of Example 3 | | | | | | |
|---|---|---|---|---|---|---|
| Reference white paint | 6-1 | 6-2 | 6-3 | 6-4 | 6-5 | 6-6 |

TABLE VI-continued

Selection of the molecular weights adapted to the formulation of paints on the formula of Example 3

| Reference of the polymer | prior art | prior art | prior art | prior art | AE | H |
|---|---|---|---|---|---|---|
| Nature of the monomer | allyl alc. TDI C12-23OE | allyl alc. TDI C12-23OE | MAEG TDI C12-23OE | MAEG TDI C12-23OE | MAEG TDI C12-23OE | MAEG TDI C12-23OE |
| 2% viscosity 10 rpm | 4800 | 4800 | 750 | 750 | 200 | 40 |
| (cP) 100 rpm | 1380 | 1380 | 500 | 500 | 208 | 72 |
| 1% viscosity 10 rpm | 800 | 800 | 220 | 220 | 40 | 20 |
| (cP) 100 rpm | 244 | 244 | 172 | 172 | 70 | 52 |
| % dry of thickening agent/total | 0.62 | 0.25 | 0.62 | 0.17 | 0.62 | 0.62 |
| pH | 8.6 | 8.6 | 8.6 | 8.7 | 8.6 | 8.7 |
| Brookfield viscosity | | | | | | |
| 24 hours 10 rpm | 27600 | 3000 | 13400 | 2500 | 7000 | 6000 |
| (cP) 100 rpm | 5250 | 950 | 5100 | 830 | 3100 | 3440 |
| Apparent viscosity (mPa.s) | 154 | 64 | 240 | 58 | 200 | 222 |
| Yield value (Pa) | 29.00 | 2.80 | 7.90 | 2.50 | 2.50 | 2.20 |
| Film tension | 0 | 3 | 2 | 3 | 3 | 3 |
| Resistance to running | 9 | 9 | 9 | 7 | 8 | 7 |
| Gloss (%) 20° | 64 | 60 | 63 | 59 | 65 | 68 |
| 60° | 85 | 82 | 81 | 80 | 83 | 85 |
| 24 hours 85° | 89 | 89 | 88 | 87 | 91 | 95 |
| Application: | | | | | | |
| brushability | C | C | C | C | A | B |
| film tension | E | B | D | C | B | B |
| covering power | C | E | A | E | A | A | allyl alc. = allyl alcohol
MAEG = ethylene glycol methacrylate
TDI = toluene diisocyanate
C12-23OE = lauryl poly(ethyleneoxy)22-ethanol This table enables the following observations:

Paints 6-1 and 6-3 (relative to the prior art) have very high viscosities at 24 hours, which create unacceptable yield values resulting in a very bad film tension (highly marked cording), although the apparent viscosity of said paints is not affected by the thickening agents used.

The formulations of paints 6-5 and 6—6 (relative to the invention), which have apparent viscosities close to those measured in the case of the prior art, distinguish themselves from the prior art by much lower viscosities at 24 hours and yield values, which greatly promote the film tension, which is an essential criterion for the application of said paints.

Formulations 6-2 (to be compared to 6-1) and 6-4 (to be compared to 6-3), which relate to the prior art, were the object of a decrease in the amount of thickening agent so as to lower the excessive viscosities at 24 hours and yield values in order to improve the film tension. However, from the results, it is apparent that the decrease in the amount of thickening agent causes a redhibitory fall in apparent viscosity and therefore in covering power.

Finally, as can be seen from U.S. Pat. No. 4,514,552, the thickening agents which are described therein have a viscosity, in aqueous solution, at a rate of 1% at 10 rpm, better than or equal to 178 centipoises, while the viscosity of solutions of copolymers in accordance with the invention under the same conditions is, as indicated in Table VI, at most 40 centipoises.

Therefore, it is confirmed that the average molecular weights of the thickening agents must not exceed a value limit, represented by the viscosity measured, in accordance with the above-identified conditions, at a rate of 2% of said agent, which is 220 centipoises at 100 rpm, in order that the thickening agents, which are the objects of the invention, confer simultaneously to the paints in which they are used a good rheological compromise at high and low shearings, resulting simultaneously in good covering power and an excellent film tension, which criteria are never achieved for the paints formulated using this type of thickening agent belonging to the prior art.

EXAMPLE 7

The object of this example is to confirm the influence of the molecular weight of the thickening agent on its ability to be used in formulations of gloss aqueous paints based, not on Primal HG 74 as in Example 6, but based on Neocryl XK 76 sold by Polyvinyl Chemie.

The paints tested were prepared in accordance quantitatively and qualitatively with test 5-1 of Example 5, except for the type of thickening agent and for the amount in which it was used in said paints.

Paints 7-1 and 7-3 (of the prior art) and 7-5 and 7-6 (objects of the invention) used different thickening agents in the same amount.

Paints 7-2 and 7-4 (of the prior art) used different thickening agents in lower amounts than for the other paints.

The results relative to the above-identified paints and to the tests carried out on said paints, such as they are defined in Example 3, are assembled in Table VII.

TABLE VII

Selection of the molecular weights adapted to the formulation of paints on the formula of Example 5

| Reference white paint | 7-1 | 7-2 | 7-3 | 7-4 | 7-5 | 7-6 |
|---|---|---|---|---|---|---|
| Reference of the polymer | prior art | prior art | prior art | prior art | AE | H |
| Nature of the monomer | allyl alc. | allyl alc. | MAEG | MAEG | MAEG | MAEG |

TABLE VII-continued

Selection of the molecular weights adapted to the formulation of paints on the formula of Example 5

|  | TDI C12-23OE | TDI C12-23OE | TDI C12-23OE | TDI C12-23OE | TDI C12-23OE | TDI C12-23OE |
|---|---|---|---|---|---|---|
| 2% viscosity 10 rpm | 4800 | 4800 | 750 | 750 | 200 | 40 |
| (cP) 100 rpm | 1380 | 1380 | 500 | 500 | 208 | 72 |
| 1% viscosity 10 rpm | 800 | 800 | 220 | 220 | 40 | 20 |
| (cP) 100 rpm | 244 | 244 | 172 | 172 | 70 | 52 |
| % dry of thickening agent/total | 1.10 | 0.39 | 1.10 | 0.32 | 1.10 | 1.10 |
| pH | 8.6 | 8.6 | 8.6 8.7 | 8.6 | 8.7 |  |
| Brookfield viscosity |  |  |  |  |  |  |
| 24 hours 10 rpm | 59000 | 4500 | 16500 | 4200 | 4500 | 3600 |
| (cP) 100 rpm | 13200 | 1200 | 6650 | 1050 | 2860 | 2320 |
| Apparent viscosity (mPa.s) | 275 | 69 | 361 | 71 | 271 | 245 |
| Yield value (Pa) | Unmeasurable | 2.50 | 11.70 | 3.40 | 2.50 | 1.50 |
| Film tension | 0 | 3 | 1 | 3 | 3 | 3 |
| Sag resistance | 9 | 9 | 9 | 7 | 8 | 6 |
| Gloss (%) 20° | 55 | 51 | 54 | 50 | 53 | 54 |
| 60° | 72 | 71 | 74 | 72 | 75 | 76 |
| 24 hours 85° | 84 | 82 | 87 | 85 | 89 | 88 |
| Application: |  |  |  |  |  |  |
| brushability | E | D | C | D | A | A |
| film tension | E | B | D | C | B | A |
| covering power | A | E | B | E | A | A | allyl alc. = allyl alcohol
MAEG = ethylene glycol methacrylate
TDI = toluene diisocyanate
C12-23OE = lauryl poly(ethyleneoxy)22-ethanol This table leads to the following observations. As in Example 6, the thickening agents used in paints 7-1 and 7-3 confer on them a very high viscosity at 24 hours and a very high yield value, resulting in a very bad film tension (highly marked cording), while the apparent viscosity of said formulations is not affected by the thickening agents used.

These same thickening agents used in a lesser amount (7-2 and 7-4) lead to acceptable viscosities at 24 hours and yield values, improving the film tension but destroying the apparent viscosity and, therefore, the covering power during application.

The thickening agents objects of the invention corresponding, in accordance with the invention, to the selective limits of molecular weights, confer on the paint formulations in which they are used an excellent rheological compromise at high and low shearings, resulting simultaneously in good covering power and good film tension, as has already been noted in Example 6.

EXAMPLE 8

The object of this example is to show the superiority of the associative thickening agents in accordance with the invention in relation to the thickening agents of the prior art, from the point of view of their compatibility with regard to colored, mineral or organic pigments in the form of a pigment paste.

By compatibility with regard to pigments, the totality of the following noted effects is meant:
the absence of a substantial increase in the viscosity of the paint after the addition of the pigment paste,
the absence of deterioration in film tension of the colored paint,
the absence of a phenomenon of floating pigments, resulting in their rising to the surface of the paint can.

Pigment paste is used to mean any concentrated suspension of mineral or organic pigments introduced into a white paint in order to color it.

The pigment pastes used have been described in Table VIII-A and are all currently used in the paint profession.

Thus, the white paints having at least one of the two following disadvantages:

viscosity in the can (that is, Brookfield viscosity at 24 hours) and yield value, which are too high (with, consequently, poor film tension: case of tests 3-2, 3—3, 5-3, 6-1, 6-3, 7-1 and 7-3), apparent viscosity which is too low (little covering power: case of tests 3-2, 4-2, 4-3, 5-2, 5-4, 6-2, 6-4, 7-2 and 7-4), have been removed from the coloring tests.

On the other hand, the white paints showing a good rheological compromise at high and low shearings (resulting in good covering power and good film tension) were submitted to the coloring tests.

For this purpose, the paints responding to the above-identified criteria of selection, selected from Examples 3 to 5, were colored by addition, under mechanical stirring, of 5 parts by weight of pigment paste for 100 parts by weight of white paint, with this quantity having been selected arbitrarily.

TABLE VIII-A

References of the pigment pastes

| Pigment Paste No. | Type | Commercial Reference | Company |
|---|---|---|---|
| 1 | yellow iron oxide | Telochrome TC 21 EJ 603 | Telosud |
| 2 | red iron oxide | Telochrome TC 21 ER 317 | Telosud |
| 3 | chromium yellow | Telochrome TC 21 EJ 655 | Telosud |
| 4 | phthalocyanine blue | Luconyl 6900 | BASF |
| 5 | phthalocyanine greeen | Green 8J | Astra |
| 6 | dinitraniline red | Red 2J | Astra |
| 7 | carbon black | Black V | Astra |
| 8 | hansa yellow | Yellow 10J | Astra |

The Brookfield viscosity at 24 hours of the colored paints was systematically measured with a view to noting any substantial increase in viscosity which would be detrimental to the quality of the paint and which would result in incompatibility between the thickening agent used and the pigment paste.

All the results relative to this study have been assembled in Table VIII-B and relate to the Brookfield viscosity at 24 hours, the possible floating of the pigments and the quality of the color development.

were shown in general to be very mediocre whatever the thickening agent used, as has already been stated.

Thus, the maximum increases and average values in variation of viscosity show that only the colored paints containing the thickening agents in accordance with the invention are not subject to a redhibitory increase in viscosity in relation to the original white paint.

TABLE VIII-B

Compatibility of thickening agents/pigmentary pastes

| Binder | Neocryl XK76 | Neocryl XK76 | Primal HG74 | Primal HG74 | Mowilith LDM7770 | Mowilith LDM7770 | Mowilith LDM7770 |
|---|---|---|---|---|---|---|---|
| Thickening agent | H | alpha | H | alpha | H | alpha | gamma |
| Dose (a) | 1.10 | 1.10 | 0.82 | 0.82 | 0.58 | 0.58 | 0.58 |
| Reference white paint | 5-6 | 5-1 | 3-4 | 3-1 | 4-4 | 4-3 | 4-1 |
| Brookfield viscosity (cP) 10 rpm 24 hours 100 rpm | | | | | | | |
| White paint | 3600 | 5000 | 7200 | 2800 | 6000 | 2600 | 4800 |
| | 2320 | 1720 | 3800 | 1440 | 2840 | 1280 | 1440 |
| Paste No. | | | | | | | |
| 1 | 4000 | 5600 * | 7600 | 2800 | 6800 * | 2800 * | 4400 * |
| | 2320 | 2080 $ | 4300 | 1600 | 3440 $ | 1520 | 1480 |
| 2 | 3000 | 5200 * | 6800 | 2800 | 6400 * | 2600 * | 4400 |
| | 1960 | 1960 | 3600 $ | 1400 | 2880 | 1320 | 1400 |
| 3 | 3600 | 9200 | 5600 | 3400 | 5600 | 3600 | 6000 |
| | 1960 | 2600 | 3080 $ | 1560 | 2600 | 1680 | 1720 |
| 4 | 5600 | 13200 * | 7200 | 10400 * | 4800 | 4800 | 7200 * |
| | 2640 | 3280 | 3720 | 2320 | 1840 | 1840 | 2360 |
| 5 | 4000 | 12400 | 6000 | 6000 * | 4000 | 3400 | 7200 |
| | 1920 | 2720 | 2880 | 1960 | 2080 | 1520 | 1960 |
| 6 | 3200 | 10400 | 3600 | 10000 | 3200 | 4800 | 6400 |
| | 1760 | 2720 | 2200 | 2080 | 1480 $ | 1440 | 1680 |
| 7 | 16000 | 20400 | 11400 | 15600 | 5200 | 6000 | 10800 |
| | 3400 | 3640 | 3880 $ | 2920 | 2360 $ | 2040 | 2600 |
| 8 | 4000 | 11200 | 8400 | 4800 | 8000 | 4800 | 6800 |
| | 2400 $ | 3000 | 4700 $ | 1840 | 3560 $ | 1840 | 2160 |
| Maximum increase viscosity 10 rpm | 2000 | 8200 | 1200 | 7600 | 2000 | 3400 | 2400 |
| Average variation viscosity 10 rpm | +250 | +4600 | −1000 | +2400 | −600 | +1200 | +1200 |

(a) % dry/total formula
* pigment flotation
$ excellent color development

The following noticeable observations are apparent from this table:

in the case of paints colored using pigment paste No. 7, the results are shown to be mediocre, except in one case (white paint 4—4, colored with pigment paste No. 7), except for paints formulated using pigment paste No. 7, the paints colored and thickened using the thickening agent in accordance with the invention show:

* very few cases of pigment flotation,

* a color development at least always equivalent to and often better than that obtained with the paints containing the prior art thickening agents with identical binding agents and pigment pastes,

* finally and particularly, a remarkable absence of redhibitory increase in Brookfield viscosity at 24 hours.

To illustrate the remarkable absence of redhibitory increase of said viscosity, Table VIII-B gives, in the last two lines:

the maximum increase in the Brookfield viscosity at 10 rpm in relation to the white paint, the average algebraic value of the variation of said viscosity. The calculations were carried out excluding the results obtained with pigment paste No. 7 which Obviously, numerous modifications and variations of the present invention are possible in light of the above teachings. It is therefore to be understood that within the scope of the appended claims, the invention may be practiced otherwise than as specifically described herein.

WHAT IS CLAIMED AS NEW AND DESIRED TO BE SECURED BY LETTERS PATENT OF THE UNITED STATES IS:

1. A copolymer which is water soluble in a neutral or an alkaline medium and which is composed of:
   (a) at least one monomer having an ethylenic unsaturation site and at least one carboxylic function;
   (b) at least one monomer having an ethylenic unsaturation site and no carboxylic function; and
   (c) at least one surfactant monomer having at least one urethane function resulting from the reaction of an isocyanate with an ethylenic unsaturation site with a surfactant compound having a hydroxyl function which is reactive with regard to the —NCO group,
   wherein said copolymer, when placed in an aqueous solution with 2% by weight of dry material and brought to a pH of 9 by the addition of ammonia, at a temperature of 20° C., has a Brookfield viscosity at 100 revolutions per minute of at most equal to 220 centipoises.

2. The copolymer of claim 1, wherein said monomer (a) is at least one member selected from the group consisting of acrylic acid, methacrylic acid, crotonic acid, cinnamic acid, itaconic acid, fumaric acid, maleic acid, citraconic acid, maleic anhydride and the $C_{1-4}$ hemiesters of itaconic acid, fumaric acid, maleic acid and citraconic acid.

3. The copolymer of claim 1, wherein said monomer (a) is acrylic acid, methacrylic acid or itaconic acid.

4. The copolymer of claim 1, wherein said monomer (b) is at least one member selected from the group consisting of methyl, ethyl, butyl, 2-ethylhexyl and lauryl acrylates and methacrylates; ethylene glycol, propylene glycol, polyethylene glycol and polypropylene glycol acrylates and methacrylates, and their corresponding phosphates and sulfates, acrylonitrile, acrylamide, n-methylolacrylamide, dimethylaminoethyl acrylates and methacrylates, allyl alcohol, vinyl acetate, sulfonic propane acrylamidomethyl acid, styrene and methylstyrene.

5. The copolymer of claim 1, wherein said monomer (b) is one member selected from the group consisting of $C_{1-4}$ acrylates and methacrylates.

6. The copolymer of claim 1, wherein said isocyanate with ethylenic unsaturation is obtained from the reaction of a diisocyanate and an ethylenic compound containing a function which is reactive with —NCO groups.

7. The copolymer of claim 6, wherein said diisocyanate is one member selected from the group consisting of 1,4-tetramethylene diisocyanate, 1,6-hexamethylene diisocyanate, 2,2,4-trimethyl-1,6 -diisocyanatohexane, 1,10-decamethylene diisocyanate, 4,4-methylene-bis-(isocyanatocyclohexane), 1,4-cyclohexylene diisocyanate, 1-isocyanato-3-isocyanatomethyl-3,5,5-trimethylcyclohexane, m- and p-phenylene diisocyanate, 2,4 and 2,6 toluene diisocyanate, xylene diisocyanate, 4-chloro-1,3-phenylene diisocyanate, 4,4'-methylene diphenylisocyanate, 1,5-naphthalene diisocyanate and tetrahydronaphthylene diisocyanate.

8. The copolymer of claim 6, wherein said ethylenic compound containing a function which is reactive with —NCO groups is one member selected from the group consisting of ethylene glycol, propylene glycol, polyethylene glycol and polypropylene glycol acrylates and methacrylates, allyl alcohol, allylamine, methallylamine and orthoallylphenol.

9. The copolymer of claim 1, wherein said surfactant compound is a compound of the formula:

$$R_1-(O-R_2-)_n-OH$$

wherein:
(i) (O—$R_2$) is ethylene oxide, propylene oxide, butylene oxide or a combination of at least two of these oxygenated groups,
(ii) n represents the average number of group (O—$R_2$) present in said surfactant compound and is a number of between 5 and 150, and
(iii) $R_1$ contains 1 to 32 carbon atoms and is one member selected from the group consisting of hydrocarbon and amines chemical structures.

10. The copolymer of claim 9, wherein $R_1$ is one radical selected from the group consisting of aliphatic and cycloaliphatic alkyls, substituted and unsubstituted aryls, polyaryls, and secondary amines of the formula $(R_3)(R_4)N-$, wherein $R_3$ and $R_4$ are hydrocarbon groups containing 1 to 20 carbon atoms.

11. The copolymer of claim 9, wherein $R_1$ is one member selected from the group consisting of $C_{12-30}$ hydrocarbon chains, —O—$R_2$ is one member selected from the group consisting of ethylene and propylene oxides, and n is from 15 to 50.

12. The copolymer of claim 9, wherein the surfactant compound is at least one member selected from the group consisting of ethoxylated dilaurylamines, ethoxylated octyl and nonyl phenols, oxyethylated lauric, stearic and cetyl alcohols, ethoxylated mono-, di- and tri-styryl phenols, in combination or alone.

13. The copolymer of claim 1, characterized in that it contains, expressed as a percentage by weight:
(i) from 15 to 75% of said monomer (a);
(ii) from 25 to 70% of said monomer (b;; and
(iii) from 0.5 to 35% of said surfactant monomer (c).

14. The copolymer of claim 1, characterized in that it contains, expressed as a percentage by weight:
(i) from 30 to 45% of said monomer (a);
(ii) from 45 to 60% of said monomer (b); and
(iii) from 4 to 15% of said surfactant monomer (c).

15. The copolymer of claim 1, characterized in that it is at least partially neutralized.

16. The copolymer of claim 15, wherein the neutralization agent is lithium, sodium, potassium, ammonium, calcium or magnesium hydroxide or an amine, taken alone or in combination.

* * * * *